(12) United States Patent
Jager et al.

(10) Patent No.: US 6,448,073 B1
(45) Date of Patent: Sep. 10, 2002

(54) ISOLATED NUCLEIC ACID MOLECULES ENCODING CANCER ASSOCIATED ANTIGENS, THE ANTIGENS PER SE, AND USES THEREOF

(75) Inventors: Dirk Jager; Elizabeth Stockert; Matthew Scanlan; Ali Gure, all of New York, NY (US); Elke Jager; Alexander Knuth, both of Frankfurt am Main (DE); Lloyd Old; Yao-tseng Chen, both of New York, NY (US)

(73) Assignee: Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/493,914

(22) Filed: Jan. 28, 2000

(51) Int. Cl.⁷ .......................... C12N 15/63; C12N 5/00; C12N 1/20; C07H 21/04
(52) U.S. Cl. .................. 435/320.1; 435/252.3; 435/325; 435/366; 536/23.1; 536/23.5; 536/24.5
(58) Field of Search ............... 536/23.1, 23.5, 536/24.5; 435/320.1, 325, 366, 252.3

(56) References Cited

FOREIGN PATENT DOCUMENTS

WO   WO9818942   *   5/1998

OTHER PUBLICATIONS

Pfreundschuh, M., "Exploitation of the B cell repertoire for the identification of human tumor antigens", Cancer Chemother Pharmacol, 2000, vol. 46, suppl., pp. S3–S7.*
Obata et al., "SEREX analysis of gastric cancer antigens", Cancer Chemother Pharmacol, 2000, vol. 26, suppl., pp. S37–S42.*
Bowie et al "Deciphering the Message in protein Sequences:Tolerance to Amino Acid substitutions" Science, vol. 247, pp. 1306–1310, 1990.*
Lazar et al, "Transforming Growth Factor Alpha: Mutation of Aspartic Acid 47 and Leuine 48 Results in Different Biological Activities", Molecular and Cellular Biology, vol. 8, pp. 1247–1252, 1988.*
Burgess et al "Possible Dissociation of the Heparin–binding and Mitogenic Acitivies of Heparin–binding Growth Factor–1 from Its Receptor–binding Activities by Site–directed Mutagenesis of a single Lysine Residue", Journal of Cellular biology, vol. 111, pp 1990.*
P. Bork, "Powers and pitfalls in sequence analysis", Genome Research, vol. 10, pp. 398–400, 2000.*
Paul, W.E., ed., Fundamental Immunology (Textbook), 3rd edition, pp. 249–251, 1993.*
Klein, J. "Self–nonself discrimination, histoincompatability, and the concept of immunology" Immunogenetics, vol. 50, pp. 116–123, 1999.*
Ristori et al "Compostional bias and mimicry toward the nonself proteome in immunodominat T cell epitopes of sel and nonself" FASEB Journal, vol. 14, pp. 431–438, 2000.*
Alberts et al, Ed., Molecular Biology of the Cell (textbook) 3rd edition, p. 465, 1994.*
Shantz and Pegg, "Translational regulation of ornithine decarboxylase and other enzymes", International J of Biochemistry and Cell Biology, vol. 31, pp. 107–122, 1999.*
McClean and Hill, "Evidence of post–translational regulation of p–glycoprotein", European J. of Cancer, vol. 29A, pp. 2243–2248, 1993.*
Fu et al, "Translational regulation of human p53 gene expression", EMBO, vol. 15, pp. 4392–4401, 1996.*
Accession No. W42096, Sep. 1998.*

\* cited by examiner

Primary Examiner—Anthony C. Caputa
Assistant Examiner—Karen A. Canella
(74) Attorney, Agent, or Firm—Fulbright & Jaworski LLP.

(57) ABSTRACT

The invention relates to isolated, cancer associated antigens, nucleic acid molecules, and various uses thereof.

25 Claims, No Drawings

ISOLATED NUCLEIC ACID MOLECULES ENCODING CANCER ASSOCIATED ANTIGENS, THE ANTIGENS PER SE, AND USES THEREOF

FIELD OF THE INVENTION

This invention relates to antigens associated with cancer, the nucleic acid molecules encoding them, as well as the uses of these.

BACKGROUND AND PRIOR ART

It is fairly well established that many pathological conditions, such as infections, cancer, autoimmune disorders, etc., are characterized by the inappropriate expression of certain molecules. These molecules thus serve as "markers" for a particular pathological or abnormal condition. Apart from their use as diagnostic "targets", i.e., materials to be identified to diagnose these abnormal conditions, the molecules serve as reagents which can be used to generate diagnostic and/or therapeutic agents. A by no means limiting example of this is the use of cancer markers to produce antibodies specific to a particular marker. Yet another non-limiting example is the use of a peptide which complexes with an MHC molecule, to generate cytolytic T cells against abnormal cells.

Preparation of such materials, of course, presupposes a source of the reagents used to generate these. Purification from cells is one laborious, far from sure method of doing so. Another preferred method is the isolation of nucleic acid molecules which encode a particular marker, followed by the use of the isolated encoding molecule to express the desired molecule.

Two basic strategies have been employed for the detection of such antigens, in e.g., human tumors. These will be referred to as the genetic approach and the biochemical approach. The genetic approach is exemplified by, e.g., dePlaen et al., Proc. Natl. Sci. USA 85: 2275 (1988), incorporated by reference. In this approach, several hundred pools of plasmids of a cDNA library obtained from a tumor are transfected into recipient cells, such as COS cells, or into antigen-negative variants of tumor cell lines which are tested for the expression of the specific antigen. The biochemical approach, exemplified by, e.g., O. Mandelboim, et al., Nature 369: 69 (1994) incorporated by reference, is based on acidic elution of peptides which have bound to MHC-class I molecules of tumor cells, followed by reversed-phase high performance liquid chromatography (HPLC). Antigenic peptides are identified after they bind to empty MHC-class I molecules of mutant cell lines, defective in antigen processing, and induce specific reactions with cytotoxic T-lymphocytes. These reactions include induction of CTL proliferation, TNF release, and lysis of target cells, measurable in an MTT assay, or a $^{51}$Cr release assay.

These two approaches to the molecular definition of antigens have the following disadvantages: first, they are enormously cumbersome, time-consuming and expensive; and second, they depend on the establishment of cytotoxic T cell lines (CTLs) with predefined specificity.

The problems inherent to the two known approaches for the identification and molecular definition of antigens is best demonstrated by the fact that both methods have, so far, succeeded in defining only very few new antigens in human tumors. See, e.g., van der Bruggen et al., Science 254: 1643–1647 (1991); Brichard et al., J. Exp. Med. 178: 489–495 (1993); Coulie, et al., J. Exp. Med. 180: 35–42 (1994); Kawakami, et al., Proc. Natl. Acad. Sci. USA 91: 3515–3519 (1994).

Further, the methodologies described rely on the availability of established, permanent cell lines of the cancer type under consideration. It is very difficult to establish cell lines from certain cancer types, as is shown by, e.g., Oettgen, et al., Immunol. Allerg. Clin. North. Am. 10: 607–637 (1990). It is also known that some epithelial cell type cancers are poorly susceptible to CTLs in vitro, precluding routine analysis. These problems have stimulated the art to develop additional methodologies for identifying cancer associated antigens.

One key methodology is described by Sahin, et al., Proc. Natl. Acad. Sci. USA 92: 11810–11913 (1995), incorporated by reference. Also, see U.S. Pat. No. 5,698,396, and Application Ser. No. 08/479,328, filed on Jun. 7, 1995 and Jan. 3, 1996, respectively. All three of these references are incorporated by reference. To summarize, the method involves the expression of cDNA libraries in a prokaryotic host. (The libraries are secured from a tumor sample). The expressed libraries are then immunoscreened with absorbed and diluted sera, in order to detect those antigens which elicit high titer humoral responses. This methodology is known as the SEREX method ("Serological identification of antigens by Recombinant Expression Cloning"). The methodology has been employed to confirm expression of previously identified tumor associated antigens, as well as to detect new ones. See the above referenced patent applications and Sahin, et al., supra, as well as Crew, et al., EMBO J 144: 2333–2340 (1995).

This methodology has been applied to a range of tumor types, including those described by Sahin et al., supra, and Pfreundschuh, supra, as well as to esophageal cancer (Chen et al., Proc. Natl. Acad. Sci. USA 94: 1914–1918 (1997)); lung cancer (Gure et al., Cancer Res. 58: 1034–1041 (1998)); colon cancer (Serial No. 08/948,705 filed Oct. 10, 1997) incorporated by reference, and so forth. Among the antigens identified via SEREX are the SSX2 molecule (Sahin et al., Proc. Natl. Acad. Sci. USA 92: 11810–11813 (1995); Tureci et al., Cancer Res. 56: 4766–4772 (1996); NY-ESO-1 Chen, et al., Proc. Natl. Acad. Sci. USA 94: 1914–1918 (1997); and SCP1 (Ser. No. 08/892,705 filed Jul. 15, 1997) incorporated by reference. Analysis of SEREX identified antigens has shown overlap between SEREX defined and CTL defined antigens. MAGE-1, tyrosinase, and NY-ESO-1 have all been shown to be recognized by patient antibodies as well as CTLs, showing that humoral and cell mediated responses do act in concert.

It is clear from this summary that identification of relevant antigens via SEREX is a desirable aim. In U.S. patent application Ser. No. 09/451,739, filed Nov. 30, 1999 and incorporated by reference, various antigens have been identified, and nucleic acid molecules encoding these have been isolated. The inventors have applied the methodologies described supra and have identified several new antigens associated with cancer, as detailed in the description which follows.

DETAILED DESCRIPTION OF PREFERRED EMBODIMENTS

EXAMPLE 1

Cell line Mz19 was used in this example. It was derived from a melanoma patient, from whom the autologous serum referred to infra was also taken. Total RNA was extracted from cell samples, using standard CsCl guanidine isothiocyanate gradient methodologies. A cDNA library was prepared, in λ ZAP, following standard methods. The resulting library of 7×10⁵ primary clones was then analyzed using the SEREX methodology of, e.g., Sahin, et al., Proc. Natl. Acad. Sci. USA 92:11810–11813;(1995); Chen, et al., Proc. Nat. Acad. Sci. USA 94: 1914–1918 (1997), and Pfreundschuh, U.S. Pat. No. 5,698,396. These references are all incorporated by reference in their entirety. To elaborate, autologous serum samples were diluted 1:10, preadsorbed with lysates of *E. coli* that had been transfected with λ ZAP, further diluted to 1:200, and were then incubated overnight at room temperature, with nitrocellulose membranes containing phage plaques at a density of about 4–5000 pfus per 130 mm plate.

The filters were washed, and then incubated with alkaline phosphatase conjugated, goat anti-human Fc γ secondary antibodies. Reactive phage plaques were visualized via incubation with 5-bromo-4-chloro-3-indolyl phosphate and nitroblue tetrazolium.

A total of 64 immunoreactive clones were identified. These were subcloned, purified, and in vivo excised to pBK-CMV plasmid. Plasmids were amplified, and DNA inserts were evaluated via EcoRI-Xba I restriction mapping. Clones which represented different cDNA molecules based upon the mapping were sequenced using standard methodologies.

Analysis showed that 43 different genes were represented in the positives. Of these, 29 were identical to, or highly homologous with, entries in GENBANK. The remaining 14 of these did not show homology with GENBANK sequences, but shared segments of identical sequences of ESTs found in different issues.

Tables 1 and 2, which follow, summarize these results.

TABLE 1

Known genes identified by autologous SEREX screening of Mz19 cDNA library

| Designation | # of clones | GenBank # | Gene |
|---|---|---|---|
| NY-MEL-1 | 1 | [M94043] | rab-related GTP-binding protein homolog |
| NY-MEL-2 | 1 | [AF109718] | subtelomeric region chromosome 3 |
| NY-MEL-3 | 1 | [AF111423] | XCAP-G homolog |
| NY-MEL-4 | 1 | [D26156] | transcriptional activator hSNF2b |
| NY-MEL-5 | 3 | [NM002415] | macrophage migration inhibiting factor |
| NY-MEL-6 | 1 | [AF047826] | cadherin 7 |
| NY-MEL-7 | 1 | [AF091083] | clone 628, chromosome X |
| NY-MEL-8 | 2 | [NM000362] | tissue inhibitor of metallo-proteinase-3 |
| NY-MEL-9 | 1 | [NM004039] | lipocortin II |
| NY-MEL-10 | 1 | [AB002374] | KIAA 0376 |
| NY-MEL-11 | 1 | [NM002574] | proliferation associated gene |
| NY-MEL-12 | 2 | [NM006141] | dynein light intermediate chain 2 |
| NY-MEL-13 | 1 | [NM001019] | ribosomal protein S15a |
| NY-MEL-14 | 1 | [Z21852] | HERV-K LTR |
| NY-MEL-15 | 1 | [X15183] | HSP 90 |
| NY-MEL-16 | 1 | [D80012] | KIAA 0190 |
| NY-MEL-17 | 1 | [X07270] | HSP 86 |
| NY-MEL-18 | 1 | [L07872] | JK-recombination signal binding protein |
| NY-MEL-19 | 1 | [NM006227] | phospholipid transfer protein |
| NY-MEL-20 | 4 | [NM004401] | DNA fragmentation factor, 45 kDa, alpha-subunit |
| NY-MEL-21 | 1 | [L22154] | ribosomal protein L37a |
| NY-MEL-22 | 1 | [NM006395] | ubiquitin activating enzyme E1 like protein |
| NY-MEL-23 | 1 | [NM001064] | transketolase |
| NY-MEL-24 | 9 | [U11687] | 30S ribosomal protein S1 homolog |
| NY-MEL-25 | 1 | [NM000994] | ribosomal protein L32 |
| NY-MEL-26 | 1 | [Z71183] | cosmid N28H9 chromosome 22q11.2 |

TABLE 1-continued

Known genes identified by autologous SEREX screening of Mz19 cDNA library

| Designation | # of clones | GenBank # | Gene |
|---|---|---|---|
| NY-MEL-27 | 1 | [AF054183] | GTP binding protein mRNA |
| NY-MEL-28 | 1 | [NM000358] | TGF-beta induced gene product |
| NY-MEL-29 | 1 | [AF090384] | SUMO-1 |

TABLE 2

Unknown genes identified by autologous SEREX screening of Mz19 cDNA library

| Designation | # of clones | EST sources/RT-PCR results |
|---|---|---|
| NY-MEL-30 | 4 | EST: total fetus, melanocytes; RT-PCR: ubiquitous |
| NY-MEL-31 | 1 | EST: brain, mammary gland, parathyroid tumor, colon, MS; RT-PCR: ubiquitous |
| NY-MEL-32 | 1 | EST: brain, pregnant uterus; RT-PCR: ubiquitous |
| NY-MEL-33 | 1 | EST: tonsils (germinal center B cell enriched), melanocytes; RT-PCR: ubiquitous |
| NY-MEL-34 | 1 | EST: pregnant uterus, infant brain, fetal heart, CLL, eye, aorta, breast |
| NY-MEL-35 | 1 | EST: melanocytes, Wilm's tumor, tonsil, adrenal gland, fetal spleen |
| NY-MEL-36 | 1 | EST: prostate, fetal liver, colon tumor |
| NY-MEL-37 | 1 | EST: cerebellum, mouse skin, mouse mammary gland |
| NY-MEL-38 | 1 | EST: HeLa cells, mouse liver |
| NY-MEL-39 | 1 | EST: colon, ovarian cancer, testis, fibroblast |
| NY-MEL-40 | 1 | EST: brain, retina, placenta, prostate cancer, pregnant uterus |
| NY-MEL-41 | 1 | EST: spleen, neuron, liver, Wilm's tumor |
| NY-MEL-42 | 1 | EST: kidney, melanocytes, breast, testis |
| NY-MEL-43 | 1 | EST: pregnant uterus, glioblastoma, pancreatic islets |

EXAMPLE 2

The genes identified as NY-MEL-8 through NY-MEL-29 in table 1, supra, are known to be expressed over a wide range of human issues. Ten of the fourteen unknown genes exhibit ESTs isolated from several normal tissues, which suggests ubiquitous mRNA expression in adult tissues. Expression of the remaining seven known genes (MEL1–7) and the 4 unknown genes (MEL30–33) was evaluated further. To do this, gene specific oligonucleotide primers were designed based upon the sequence information. The primers were also designed to amplify segments 300–600 base pairs in length, with primer melting temperatures of about 65–70° C. RT-PCR was then carried out using 30 amplification cycles, at an annealing temperature of 60° C. Products were analyzed by 1.5% gel electrophoresis, and ethidium bromide visualization. Five representative normal tissues were analyzed (brain, colon, kidney, testis, liver), with isolated clones serving as positive controls.

The results indicated that the four unknown genes were expressed universally, at similar levels. Of the 7 known genes, 5 of these (MEL-2, and MEL4–7) showed universal expression at similar levels. Two of the genes, i.e., those identified as MEL-1 and MEL-3, showed differentiated tissue expression. Specifically, MEL-1 (SEQ ID NO: 1 hereafter) gave a strong RT-PCR signal in melanoma line Mz19, weaker signals in testis and cancer, and was negative in brain, colon and liver. The gene represented by MEL-3 (SEQ ID NO: 2 hereafter) gave a strong RT-PCR signal in testis only, with weak, albeit positive signals, in brain, colon, liver and kidney.

EXAMPLE 3

The mRNA expression of SEQ ID NO: 1 suggested further evaluation in a larger panel of normal tissues. This was carried out via Northern blot analyses. Commercially available poly A (2 μg/lane) multiple human tissue Northern blotting kits were used. Blotting was carried out using randomly primed, $^{32}$p labelled probes, based upon the PCR products described supra. Hybridization took place for 60 minutes at 68° C., followed by a high stringency wash (40 minutes, 2×SSC/0.05% SDS at room temperature, followed by 40 minutes in 0.1×SSC/0.1% SDS at 50° C.), followed by autoradiography. Northern blotting was also carried out on different melanoma cell lines, using 10 μg/ lane of total RNA.

No visible signal-was found in any of the 17 normal tissue samples tested. When expression in cells of melanocytic lineage was examined, a strong signal was found for an mRNA species of about 1.6 kilobases in cultured melanocytes, and variable, weaker signals in five of seven melanoma cell lines tested. The predominant expression suggested than SEQ ID NO: 1 encodes a melanocyte differentiation antigen.

EXAMPLE 4

The results developed supra suggested than a simpler method for typing for expression of SEQ ID NO:1 in tumor samples was warranted. Hence, an RT-PCR assay was carried out on eight melanoma cell lines, using the protocol described supra. Seven of the cell lines were positive for expression of SEQ ID NO: 1, using the standards supra. These results were compared to Northern blot analyses. Two of the lines were positive for both Northern blotting and RT-PCR. Two cultured melanocytes were also strongly positive in RT-PCR. Six breast cancer lines were negative by RT-PCR.

These results suggested that RT-PCR is more sensitive than Northern blotting for determining expression of SEQ ID NO: 1. This was confirmed when normal tissue RNA was examined via RT-PCR. Several Northern blot negative tissues gave weak to moderate signals, including testis, kidney, uterus, prostate, and pancreatic tissue. Adrenal gland, which was not included in Northern blotting work, gave a positive RT-PCR signal comparable to that for cultured melanocytes.

Following this work, a panel of tumor tissues was examined via RT-PCR, also as described supra, of nineteen melanoma tumor specimens analyzed, 17 were positive. Twelve gave a moderate to strong signal. One lung cancer sample was positive, while 4 additional lung cancer, 4 colon cancer, 4 breast cancer and 4 squamous carcinomas were negative.

Analysis of SEQ ID NO: 1 shows a 1407 base pair molecule. The first 47 5' base pairs are not translated, as is also the case for the final 724 base pairs, which are followed by a polyA sequence 4 nucleotides long. This provides an open reading frame of 636 base pairs, encoding a putative polypeptide of 211 amino acids, with a predicted molecular mass of 23,714 kilodaltons.

Protein motif analysis shows five highly conserved GTP-binding domains, typical of ras superfamily members (ras, rab, rho, ran, arf). A comparison with the GENBANK database confirmed homology to rat, rab-related GTP binding protein, with 81.5% identity at the nucleotide level, and 97% identity at the amino acid level.

With respect to human molecules, SEQ ID NO: 1 is closest in identity to rab 32 (GENBANK NM006834), with 75% amino acid identity, and 88% homology when standard conservative changes are made.

The protein encoded by SEQ ID NO: 1 (SEQ ID NO: 3 gives its amino acid sequence), is unique in its carboxy terminus. Generally, rab proteins terminate in a "CC", "CXC" or "CCXX" motif, which permits posttranslational lipid modification, probably as geranylgeranyl prenylation of the cysteine residues. This hydrophobic modification is functionally crucial for interaction with lipid membranes. The amino acid sequence of SEQ ID NO: 3, however, terminated with CSGCAKS (residues 205–211 of SEQ ID NO:3); which more resembles a ras protein than a rab protein. This suggests a different lipid modification pattern, probably farnesyl prenylation at carboxy terminal cysteine, and palmitoylation at the upstream cysteine. See, e.g., Der, Meth. Enzymol 255: 46–60 (1995).

EXAMPLE 5

SEQ ID NO: 2, as reported supra, also showed differential expression. Analysis of this molecule shows a 3198 base pair cDNA, of which 68 base pairs at the 5' end, and 82 at the 3' end are untranslated. The untranslated 3' end is followed by a 44 nucleotide polyA sequence. The ORF extends for 3048 base pairs, encoding a polypeptide of 1015 amino acids with calculated molecular weight of 114.3 k Da.

A homology search showed SEQ ID NO: 2 to be the human counterpart of X. laevis chromosome associated polypeptide group G (Genbank Accession No. AF111423). This molecule is a chromosome condensation protein, which is part of the 13S condensin complex formed during early stages of mitosis. SEQ ID NO: 2 shows 28% nucleotide identity with AF 111423, and 59% amino acid identity.

When expression of SEQ ID NO: 2 was evaluated via RT-PCR and Northern blotting, as described supra, the strongest Northern blotting signal was found in testis, and a weak signal was found in thymus. No other signals were found in normal tissues. Melanoma lines showed variable signals of weak to moderate intensity.

When RT-PCR results were studied, all RNA of Northern blot positive samples tested were positive, with highest expression in testis.

The foregoing examples describe the isolation of nucleic acid molecules which encode a cancer associated antigen. "Associated" is used herein because while it is clear that the relevant molecule was expressed by several types of cancer, other cancers, not screened herein, may also express the antigen.

The invention relates to nucleic acid molecules which encode the antigens encoded by, e.g., SEQ ID NOS: 1 and 2, as well as the antigens encoded thereby, such as the proteins with the amino acid sequences of SEQ ID NO: 3, and that encoded by the reading frame of SEQ ID NO: 2, as discussed supra. It is to be understood that all sequences which encode the recited antigen are a part of the invention.

Also a part of the invention are those isolated molecules which hybridize under stringent conditions to SEQ ID NO: 2, or those which both hybridize to SEQ ID NO: 1, under stringent conditions and encode a protein which has, at its C terminus, the amino acid sequence CSGCAKS. "Stringent conditions", as used herein, refers to conditions at least as stringent as those referred to in , e.g., U.S. Pat. No. 5,342, 774, at example 29, the disclosure of which is incorporated by reference.

Also a part of the invention are expression vectors which incorporate the nucleic acid molecules of the invention, in operable linkage (i.e., "operably linked") to a promoter. Construction of such vectors, such as viral (e.g., adenovirus or Vaccinia virus) or attenuated viral vectors is well within the skill of the art, as is the transformation or transfection of cells, to produce eukaryotic cell lines, or prokaryotic cell strains which encode the molecule of interest. Exemplary of the host cells which can be employed in this fashion are COS cells, CHO cells, yeast cells, insect cells (e.g., *Spodoptera frugiperda*), NIH 3T3 cells, and so forth. Prokaryotic cells, such as *E. coli* and other bacteria may also be used. Any of these cells can also be transformed or transfected with further nucleic acid molecules, such as those encoding cytokines, e.g., interleukins such as IL-2, 4, 6, or 12 or HLA or MHC molecules.

Also a part of the invention are the antigens described herein, both in original form and in any different post translational modified forms. The molecules are large enough to be antigenic without any posttranslational modification, and hence are useful as immunogens, when combined with an adjuvant (or without it), in both precursor and post-translationally modified forms. Antibodies produced using these antigens, both poly and monoclonal, are also a part of the invention as well as hybridomas which make monoclonal antibodies to the antigens. The whole protein can be used therapeutically, or in portions, as discussed infra. Also a part of the invention are antibodies against this antigen, be these polyclonal, monoclonal, reactive fragments, such as Fab, (F(ab)$_2$' and other fragments, as well as chimeras, humanized antibodies, recombinantly produced antibodies, and so forth.

As is clear from the disclosure, one may use the proteins and nucleic acid molecules of the invention diagnostically. The SEREX methodology discussed herein is premised on an immune response to a pathology associated antigen. Hence, one may assay for the relevant pathology via, e.g., testing a body fluid sample of a subject, such as serum, for reactivity with the antigen per se. Reactivity would be deemed indicative of possible presence of the pathology. So, too, could one assay for the expression of any of the antigens via any of the standard nucleic acid hybridization assays which are well known to the art, and need not be elaborated upon herein. One could assay for antibodies against the subject molecules, using standard immunoassays as well.

Analysis of SEQ ID NOS: 1 and 2 will show that there are 5' and 3' non-coding regions presented therein. The invention relates to those isolated nucleic acid molecules which contain at least the coding segment, and which may contain any or all of the non-coding 5' and 3' portions.

Also a part of the invention are portions of the relevant nucleic acid molecules which can be used, for example, as oligonucleotide primers and/or probes, such as one or more of:

cgaagagcag cataggaaag agttag (SEQ ID NO:4)
gacactgtgt ttcacgttgg tc (SEQ ID NO:5)

These are the oligonucleotides used in the RT-PCR experiments for amplifying SEQ ID NO: 1, described supra.

As was discussed supra, study of other members of the "CT" family reveals that these are also processed to peptides which provoke lysis by cytolytic T cells. There has been a great deal of work on motifs for various MHC or HLA molecules, which is applicable here. Hence, a further aspect of the invention is a therapeutic method, wherein one or more peptides derived from the antigens of the invention which bind to an HLA molecule on the surface of a patient's tumor cells are administered to the patient, in an amount sufficient for the peptides to bind to the MHC/HLA molecules, and provoke lysis by T cells. Any combination of peptides may be used. These peptides, which may be used alone or in combination, as well as the entire protein or immunoreactive portions thereof, may be administered to a subject in need thereof, using any of the standard types of administration, such as intravenous, intradermal, subcutaneous, oral, rectal, and transdermal administration. Standard pharmaceutical carriers, adjuvants, such as saponins, GM-CSF, and interleukins and so forth may also be used. Further, these peptides and proteins may be formulated into vaccines with the listed material, as may dendritic cells, or other cells which present relevant MHC/peptide complexes.

Similarly, the invention contemplates therapies wherein nucleic acid molecules which encode the proteins of the invention, one or more or peptides which are derived from these proteins are incorporated into a vector, such as a Vaccinia or adenovirus based vector, to render it transfectable into eukaryotic cells, such as human cells. Similarly, nucleic acid molecules which encode one or more of the peptides may be incorporated into these vectors, which are then the major constituent of nucleic acid bases therapies.

Any of these assays can also be used in progression/regression studies. One can monitor the course of abnormality involving expression of these antigens simply by monitoring levels of the protein, its expression, antibodies against it and so forth using any or all of the methods set forth supra.

It should be clear that these methodologies may also be used to track the efficacy of a therapeutic regime. Essentially, one can take a baseline value for a protein of interest using any of the assays discussed supra, administer a given therapeutic agent, and then monitor levels of the protein thereafter, observing changes in antigen levels as indicia of the efficacy of the regime.

As was indicated supra, the invention involves, inter alia, the recognition of an "integrated" immune response to the molecules of the invention. One ramification of this is the ability to monitor the course of cancer therapy. In this method, which is a part of the invention, a subject in need of the therapy receives a vaccination of a type described herein. Such a vaccination results, e.g., in a T cell response against cells presenting HLA/peptide complexes on their cells. The response also includes an antibody response, possibly a result of the release of antibody provoking proteins via the lysis of cells by the T cells. Hence, one can monitor the effect of a vaccine, by monitoring an antibody response. As is indicated, supra, an increase in antibody titer may be taken as an indicia of progress with a vaccine, and vice versa. Hence, a further aspect of the invention is a method for monitoring efficacy of a vaccine, following administration thereof, by determining levels of antibodies in the subject which are specific for the vaccine itself, or a large molecule of which the vaccine is a part.

The identification of the subject proteins as being implicated in pathological conditions such as cancer also suggests a number of therapeutic approaches in addition to those discussed supra. The experiments set forth supra establish that antibodies are produced in response to expression of the protein. Hence, a further embodiment of the invention is the treatment of conditions which are characterized by aberrant or abnormal levels of one or more of the proteins, via administration of antibodies, such as humanized antibodies, antibody fragments, and so forth. These may be tagged or labelled with appropriate cystostatic or cytotoxic reagents.

T cells may also be administered. It is to be noted that the T cells may be elicited in vitro using immune responsive cells such as dendritic cells, lymphocytes, or any other immune responsive cells, and then reperfused into the subject being treated.

Note that the generation of T cells and/or antibodies can also be accomplished by administering cells, preferably treated to be rendered non-proliferative, which present relevant T cell or B cell epitopes for response, such as the epitopes discussed supra.

The therapeutic approaches may also include antisense therapies, wherein an antisense molecule, preferably from 10 to 100 nucleotides in length, is administered to the subject either "neat" or in a carrier, such as a liposome, to facilitate incorporation into a cell, followed by inhibition of expression of the protein. Such antisense sequences may also be incorporated into appropriate vaccines, such as in viral vectors (e.g., Vaccinia), bacterial constructs, such as variants of the known BCG vaccine, and so forth.

Other features and applications of the invention will be clear to the skilled artisan, and need not be set forth herein. The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. An isolated cDNA molecule which encodes a cancer associated antigen which, when expressed in a human provokes antibodies against said cancer associated antigen, wherein said antigen has, as a C terminal amino acid sequence, CSGCAKS (resides 205–211 of SEQ ID NO:3), and wherein the complementary sequence of said isolated cDNA molecule hybridizes to SEQ ID NO: 1 under stringent conditions.

2. An isolated cDNA molecule which encodes a cancer associated antigen which, when expressed in a human, provokes antibodies against said cancer associated antigen, the complementary sequence of which hybridizes, under stringent conditions, to SEQ ID NO: 2.

3. The isolated cDNA molecule of claim 1, comprising the nucleotide sequence of SEQ ID NO: 1.

4. The isolated cDNA molecule of claim 1, comprising the nucleotide sequence defined by nucleotides 48–683 of SEQ ID NO: 1.

5. The isolated cDNA molecule of claim 1, comprising a nucleotide sequence which encodes a protein, the amino acid sequence of which is set forth at SEQ ID NO: 3.

6. The isolated cDNA molecule of claim 2, comprising the nucleotide sequence of SEQ ID NO: 2.

7. The isolated cDNA molecule of claim 2, comprising nucleotides 69–3116 of SEQ ID NO: 2.

8. The isolated cDNA molecule of claim 2, comprising a nucleotide sequence that encodes the protein encoded by nucleotides 69–3116 of SEQ ID NO: 2.

9. Expression vector comprising the isolated cDNA molecule of claim 1, operably linked to a promoter.

10. Expression vector comprising the isolated cDNA molecule of claim 2, operably linked to a promoter.

11. Eukaryotic cell line or prokaryotic cell strain, transformed or transfected with the expression vector of claim 9 or 10.

12. Eukaryotic cell line or prokaryotic cell strain, transformed or transfected with the isolated cDNA molecule of claim 1 or 2.

13. The eukaryotic cell line or prokaryotic cell strain of claim 12, wherein said cell line is also transfected with a nucleic acid molecule coding for a cytokine.

14. The eukaryotic cell line or prokaryotic cell strain of claim 13, wherein said cell line is further transfected by a nucleic acid molecule coding for an MHC molecule.

15. The eukaryotic cell line or prokaryotic cell strain of claim 13, wherein said cytokine is an interleukin.

16. The eukaryotic cell line or prokaryotic cell strain of claim 15, said interleukin is IL-2, IL-4 or IL-12.

17. The eukaryotic cell line or prokaryotic cell strain of claim 12, wherein said cell line has been rendered non-proliferative.

18. The eukaryotic cell line of claim 12, wherein said cell line is a fibroblast cell line.

19. Expression vector comprising a mutated or attenuated virus and the isolated cDNA molecule of claim 1 or 2.

20. The expression vector of claim 19, wherein said virus is adenovirus or vaccinia virus.

21. The expression vector of claim 20, wherein said virus is vaccinia virus.

22. The expression vector of claim 21, wherein said virus is adenovirus.

23. Expression system useful in transfecting a cell, comprising (i) a first vector containing a cDNA molecule which codes for the isolated cancer associated antigen encoded by SEQ ID NO: 1 and 2 and (ii) a second vector selected from the group consisting of (a) a vector containing a nucleic acid molecule which codes for an MHC or HLA molecule which presents an antigen derived from said cancer associated antigen and (b) a vector containing a nucleic acid molecule which codes for an interleukin.

24. Composition comprising an expression vector which encodes at least one peptide consisting of an amino acid sequence of at least 8 and no more than 25 amino acids concatenated to each other in the isolated cancer associated antigen encoded by the cDNA molecule of claim 1 and 2, and a pharmaceutically acceptable adjuvant.

25. The composition of claim 24, wherein said expression vector encodes a plurality of said peptides.

* * * * *

UNITED STATES PATENT AND TRADEMARK OFFICE
CERTIFICATE OF CORRECTION

PATENT NO. : 6,448,073 B1
DATED : September 10, 2002
INVENTOR(S) : D. Jager et al.

It is certified that error appears in the above-identified patent and that said Letters Patent is hereby corrected as shown below:

<u>Title page,</u>
Item [73], Assignee, should read as follows:

-- **Ludwig Institute for Cancer Research,
Memorial Sloan-Kettering Cancer Center,
Cornell Reseach Foundation** --

Signed and Sealed this

Twenty-fifth Day of March, 2003

JAMES E. ROGAN
*Director of the United States Patent and Trademark Office*

UNITED STATES PATENT AND TRADEMARK OFFICE
CERTIFICATE OF CORRECTION

PATENT NO.   : 6,448,073 B1
DATED        : September 10, 2002
INVENTOR(S)  : D. Jager et al.

It is certified that error appears in the above-identified patent and that said Letters Patent is hereby corrected as shown below:

<u>Title page,</u>
Item [73], change "Cornell Research Foundation" to -- Cornell Research Foundation, Inc. --

Signed and Sealed this

Thirteenth Day of January, 2004

JON W. DUDAS
*Acting Director of the United States Patent and Trademark Office*

SEQUENCE LISTING

<160> NUMBER OF SEQ ID NOS: 5

<210> SEQ ID NO 1
<211> LENGTH: 1407
<212> TYPE: DNA
<213> ORGANISM: Homo sapiens
<220> FEATURE:
<221> NAME/KEY: Unsure
<222> LOCATION: 1165 .. 1390

<400> SEQUENCE: 1

```
ggctgcgctt ccctggtcag gcacggcacg tctggccggc cgccaggatg caggccccgc      60
acaaggagca cctgtacaag ttgctggtga ttggcgacct gggcgtgggg aagaccagta     120
tcatcaagcg ctacgtgcac cagaacttct cctcgcacta ccgggccaca atcggcgtgg     180
acttcgcgct caaggtgctc cactgggacc cggagactgt ggtgcgcctg cagctctggg     240
atatcgcagg tcaagaaaga tttggaaaca tgacgagggt ctattaccga gaagctatgg     300
gtgcatttat tgtcttcgat gtcaccaggc cagccacatt tgaagcagtg gcaaagtgga     360
aaatgatttt ggactccaag ttaagtctcc ctaatggcaa accggtttca gtggttttgt     420
tggccaacaa atgtgaccag gggaaggatg tgctcatgaa caatggcctc aagatggacc     480
agttctgcaa ggagcacggt ttcgtaggat ggtttgaaac atcagcaaag gaaaatataa     540
acattgatga agcctccaga tgcctggtga aacacatact tgcaaatgag tgtgacctaa     600
tggagtctat tgagccggac gtcgtgaagc cccatctcac atcaaccaag gttgccagct     660
gctctggctg tgccaaatcc tagtaggcac ctttgctggt gtctggtagg aatgacctca     720
ttgttccaca aattgtgcct ctatttttac cattttgggt aaacgtcagg atagatatac     780
cacatgtggc aagccaaaga tctatgcctc tgttttttca atgagagaga aatagcaaat     840
gttctttcta tgctttcctc accatcatca cagtgtttac aaacttttga aaatatttag     900
tctgttacaa acttctgtca tgtagctgac caaaatcctg cagggccaca gtcggcactg     960
ttatttgctt cttttaatca gcaaaggcct caagtcttaa aataaagggg gagaagaaca    1020
aactagctgt caagtcaagg actggctttc accttgccct ggtgtctttt tccagatttc    1080
aatatattct ctgatggcct gacaggccta ttaagtagat gtgatatttt cttccaagat    1140
gacctccatt ctcggcagac ctaanaagtt gcctctgagt tagctctttg gaatcgngaa    1200
cacaggtgtg ctatattgnc cttgtctaac tgncacttgn catggcctga atgttggctt    1260
aactgaatat tnnatgaaaa gacatgcctt catatgtgcc tttttggtaa ctttctttga    1320
ctnaacctng gggctccttt ttcatgcttt acatgtaaaa tatatatttt tttttttgcag    1380 gggaccattn aacctttaag gataaaa                                         1407
```

<210> SEQ ID NO 2
<211> LENGTH: 3242
<212> TYPE: DNA
<213> ORGANISM: Homo sapiens
<220> FEATURE:
<221> NAME/KEY: Unsure
<222> LOCATION: 3037 .. 3198

<400> SEQUENCE: 2

| | | | | | |
|---|---|---|---|---|---|
| ctgggttggc | gggctggcag | gctgtagccg | agcgcgggca | ggactcgtcc | cggcagggtt | 60 |
| ccagagccat | gggagcggaa | aggaggctgc | tgtcgattaa | ggaggccttt | cggctggcgc | 120 |
| agcagccgca | ccagaaccag | gcgaagctgg | tggtggcgct | gagccgcacc | taccgcacga | 180 |
| tggatgataa | gacagttttt | catgaggagt | tcattcatta | ccttaaatat | gttatggtgg | 240 |
| tctataaacg | tgaaccagct | gtggagaggg | taatagaatt | tgcagcaaag | tttgttacct | 300 |
| catttcacca | atcagatatg | gaagatgatg | aggaagagga | agatggtggc | cttttaaatt | 360 |
| atttgtttac | ttttctctta | aagtctcatg | aagcaaacag | caatgcagtg | agatttagag | 420 |
| tgtgcctgct | cataaacaag | cttttgggaa | gtatgccaga | aaatgctcag | attgatgatg | 480 |
| atgtgtttga | taaaattaat | aaagccatgc | ttattagatt | gaagataag | attccaaatg | 540 |
| tgagaataca | ggcagttctg | gcgctttcac | gacttcagga | tcccaaggat | gatgaatgcc | 600 |
| cagtggttaa | tgcatatgct | actttgattg | aaaatgattc | aaatccagaa | gttagacggg | 660 |
| cagtgttatc | atgtattgca | ccatcagcaa | agactttgcc | aaaaattgta | gggcgcacca | 720 |
| aggatgtgaa | agaggctgtc | agaaagctgg | cttatcaggt | tttagctgaa | aaggttcata | 780 |
| tgagagctat | gtccattgct | cagagagtaa | tgctccttca | acaaggtctt | aatgacagat | 840 |
| cagatgctgt | gaaacaagct | atgcagaagc | atcttcttca | aggctggtta | cgggtctctg | 900 |
| aaggaaatat | cttagagttg | ctccatcggt | tggatgtaga | aaattcttct | gaagtggcag | 960 |
| tctctgttct | caatgccttg | ttttcaataa | ctcctctcag | tgaactggtg | ggactctgta | 1020 |
| aaacaatga | tggcaggaaa | ttgattccag | tggaaacatt | aactcctgaa | attgctttgt | 1080 |
| attggtgtgc | cctttgtgaa | tatttgaaat | caaaggaga | tgaaggtgaa | gaattttag | 1140 |
| agcagatttt | gccagagcct | gtagtatatg | cagactattt | attgagttac | atccagagca | 1200 |
| ttccagttgt | taatgaagaa | cacagaggtg | attttttccta | tattggaaat | tgatgacaa | 1260 |
| aagaattcat | aggtcaacaa | ttgattctaa | ttattaagtc | tttggatacc | agtgaagaag | 1320 |
| gaggaagaaa | aaaactgctg | gctgtttac | aggagattct | tattttaccc | acaatcccaa | 1380 |
| tatccctggt | ttcttttctt | gttgaaagac | tactccacat | cattatagat | gataataaga | 1440 |
| gaacacaaat | tgttacagaa | attatctcag | agattcgggc | gcccattgtt | actgttggtg | 1500 |
| ttaataacga | tccagctgat | gtaagaaaga | agaactcaa | gatggctgaa | ataaagtta | 1560 |
| agcttatcga | agccaaagaa | gctttggaaa | attgcattac | cttacaggat | tttaatcggg | 1620 |
| catcagaatt | aaaagaagaa | ataaaagcat | tagaagatgc | cagaataaac | cttttgaaag | 1680 |
| agacagagca | acttgaaatt | aaagaagtcc | acatagaaa | gaatgatgct | gaaacattgc | 1740 |
| agaaatgtct | tattttatgc | tatgaactgt | gaagcagat | gtccatttca | acaggcttaa | 1800 |
| gtgcaaccat | caatggaatc | atcgaatctt | tgattcttcc | tggaataata | agtattcatc | 1860 |
| ctgttgtaag | aaacctggct | gtttttatgct | tgggatgctg | tggactacag | aatcaggatt | 1920 |
| ttgcaaggaa | acacttcgta | ttactattgc | aggttttgca | aattgatgat | gtcacaataa | 1980 |
| aaataagtgc | tttaaaggca | atctttgacc | aactgatgac | gttcgggatt | gaaccattta | 2040 |

-continued

```
aaactaaaaa aatcaaaaca cttcattgtg aaggtacaga aataaacagt gatgatgagc   2100
aagaatcaaa agaagttgaa gagactgcta cagctaagaa tgttctgaaa ctcctttctg   2160
atttcttaga tagtgaggta tctgaactta ggactggagc tgcagaagga ctagccaagc   2220
tgatgttctc tgggcttttg gtcagcagca ggattctttc tcgtcttatt ttgttatggt   2280
acaatcctgt gactgaagag gatgttcaac ttcgacattg cctaggcgtg ttcttccccg   2340
tgtttgctta tgcaagcagg actaatcagg aatgctttga agaagctttt cttccaaccc   2400
tgcaaacact ggccaatgcc cctgcatctt ctccttagc tgaaattgat atcacaaatg    2460
ttgctgagtt acttgtagat ttgacaagac caagtggatt aaatcctcag gccaagactt   2520
cccaagatta tcaggcctta acagtacatg acaatttggc tatgaaaatt tgcaatgaga   2580
tcttaacaag tccgtgctcg ccagaaattc gagtctatac aaaagccttg agttctttag   2640
aactcagtag ccatccttgca aaagatcttc tggttctatt gaatgagatt ctggagcaag   2700 taaagatag gacatgtctg agagctttgg agaaaatcaa gattcagtta gaaaaggaa    2760 ataaagaatt tggtgaccaa gctgaagcag cacaggatgc caccttgact acaactactt   2820
tccaaaatga agatgaaaag aataaagaag tatatatgac tccactcagg ggtgtaaaag   2880
caacccaagc atcaaagtct actcagctaa agactaacag aggacagaga aaagtgacag   2940
tttcagctag gacgaacagg aggtgtcaga ctgctgaagc cgactctgaa agtgatcatg   3000
aagttccaga accagaatca gaaatgaaga tgagactncc aagacgagcc aaaaccgcag   3060
cnctanaaaa aagtaaactt anccttgccc aattttcaa tgaagattta agttaggaaa     3120
nacgatggag gnggaatcct ttaagattat gtccagttat ttgctttaat aaanaanaag   3180 ttaccttgt caaaatcnaa aaaaaaaaaa aaaaaaaaaa aaaaaaaaaa aaaaaaaaaa    3240
aa                                                                  3242
```

<210> SEQ ID NO 3
<211> LENGTH: 211
<212> TYPE: PRT
<213> ORGANISM: Homo sapiens
<220> FEATURE:

<400> SEQUENCE: 3

```
Met Gln Ala Pro His Lys Glu His Leu Tyr Lys Leu Val Ile Gly
 1               5                  10                  15

Asp Leu Gly Val Gly Lys Thr Ser Ile Ile Lys Arg Tyr Val His Gln
                20                  25                  30

Asn Phe Ser Ser His Tyr Arg Ala Thr Ile Gly Val Asp Phe Ala Leu
            35                  40                  45

Lys Val Leu His Trp Asp Pro Glu Thr Val Val Arg Leu Gln Leu Trp
        50                  55                  60

Asp Ile Ala Gly Gln Glu Arg Phe Gly Asn Met Thr Arg Val Tyr Tyr
65                  70                  75                  80

Arg Glu Ala Met Gly Ala Phe Ile Val Phe Asp Val Thr Arg Pro Ala
                85                  90                  95

Thr Phe Glu Ala Val Ala Lys Trp Lys Asn Asp Leu Asp Ser Lys Leu
            100                 105                 110

Ser Leu Pro Asn Gly Lys Pro Val Ser Val Val Leu Leu Ala Asn Lys
        115                 120                 125

Cys Asp Gln Gly Lys Asp Val Leu Met Asn Asn Gly Leu Lys Met Asp
    130                 135                 140
```

-continued

```
Gln Phe Cys Lys Glu His Gly Phe Val Gly Trp Phe Glu Thr Ser Ala
145                 150                 155                 160

Lys Glu Asn Ile Asn Ile Asp Glu Ala Ser Arg Cys Leu Val Lys His
                165                 170                 175

Ile Leu Ala Asn Glu Cys Asp Leu Met Glu Ser Ile Glu Pro Asp Val
            180                 185                 190

Val Lys Pro His Leu Thr Ser Thr Lys Val Ala Ser Cys Ser Gly Cys
        195                 200                 205

Ala Lys Ser
    210

<210> SEQ ID NO 4
<211> LENGTH: 26
<212> TYPE: DNA
<213> ORGANISM: Homo sapiens
<220> FEATURE:

<400> SEQUENCE: 4
cgaagagcag cataggaaag agttag                                      26

<210> SEQ ID NO 5
<211> LENGTH: 22
<212> TYPE: DNA
<213> ORGANISM: Homo sapiens
<220> FEATURE:

<400> SEQUENCE: 5
gacactgtgt ttcacgttgg tc                                          22
```